(12) United States Patent
Raghuveer et al.

(10) Patent No.: US 10,213,558 B2
(45) Date of Patent: Feb. 26, 2019

(54) DRUG DELIVERY DEVICE

(71) Applicant: Glenmark Pharmaceuticals S.A., La Chaux-de-Fonds (CH)

(72) Inventors: A. V. V. P. S. Raghuveer, Andhra Pradesh (IN); Rajendra Shetty, Maharashtra (IN); Prashant Navale, Maharashtra (IN)

(73) Assignee: Glenmark Pharmaceuticals S.A. (CH)

( * ) Notice: Subject to any disclaimer, the term of this patent is extended or adjusted under 35 U.S.C. 154(b) by 152 days.

(21) Appl. No.: 15/177,697

(22) Filed: Jun. 9, 2016

(65) Prior Publication Data

US 2017/0274147 A1  Sep. 28, 2017

(30) Foreign Application Priority Data

Mar. 28, 2016 (IN) .............................. 201621010632

(51) Int. Cl.
*A61M 5/315* (2006.01)
*A23K 40/00* (2016.01)
*A61M 5/31* (2006.01)

(52) U.S. Cl.
CPC ......... *A61M 5/31548* (2013.01); *A23K 40/00* (2016.05); *A61M 5/3156* (2013.01); *A61M 5/31505* (2013.01); *A61M 5/31553* (2013.01); *A61M 5/31555* (2013.01); *A61M 5/31563* (2013.01); *A61M 5/31565* (2013.01); *A61M 5/31591* (2013.01); *A61M 5/3129* (2013.01); *A61M 5/31536* (2013.01); *A61M 2005/311* (2013.01); *A61M 2005/3104* (2013.01); *A61M 2005/3125* (2013.01); *A61M 2205/583* (2013.01); *A61M 2250/00* (2013.01)

(58) Field of Classification Search
CPC .... A61M 2005/3126; A61M 2205/583; A61M 2005/3125; A61M 5/31511; A61M 2005/3139; A61M 5/31525; A61M 5/31561; A61M 5/31551; A61M 3/51555
USPC ....... 604/181, 186, 187, 189, 198, 207, 208, 604/210, 211, 218, 222, 228, 260, 506
See application file for complete search history.

(56) References Cited

U.S. PATENT DOCUMENTS

| | | | | |
|---|---|---|---|---|
| 2,648,334 A * | 8/1953 | Brown | .................... | A61M 5/24 604/205 |
| 3,815,785 A * | 6/1974 | Gilmont | .................. | A61M 3/00 222/46 |
| 5,328,486 A * | 7/1994 | Woodruff | .......... | A61M 5/31555 604/207 |
| 5,376,081 A * | 12/1994 | Sapienza | .............. | A61M 5/3129 604/186 |
| 6,764,469 B2 * | 7/2004 | Broselow | .......... | A61M 5/31525 604/207 |
| 7,329,241 B2 | 2/2008 | Horvath et al. | | |
| 2004/0186437 A1 * | 9/2004 | Frenette | .............. | A61M 5/3129 604/189 |
| 2009/0177156 A1 * | 7/2009 | MacLean | ............ | A61M 5/3148 604/135 |
| 2010/0305515 A1 | 12/2010 | Subramanian et al. | | |
| 2011/0046559 A1 * | 2/2011 | Lum | .................... | A61M 5/3137 604/189 |

(Continued)

*Primary Examiner* — Bradley J Osinski
(74) *Attorney, Agent, or Firm* — Ryan, Mason & Lewis, LLP

(57) ABSTRACT

Disclosed herein is a syringe device comprises (a) an outer housing, (b) a barrel, (c) a stopper, and (d) a plunger with one or more grooves.

20 Claims, 10 Drawing Sheets

(56) References Cited

U.S. PATENT DOCUMENTS

| | | | | |
|---|---|---|---|---|
| 2011/0313397 A1* | 12/2011 | Gold | ............... | A61M 5/31551 |
| | | | | 604/506 |
| 2012/0046613 A1* | 2/2012 | Plumptre | ........... | A61M 5/31511 |
| | | | | 604/189 |
| 2014/0288506 A1* | 9/2014 | Mumford | ............... | A61M 5/31 |
| | | | | 604/207 |
| 2016/0220761 A1* | 8/2016 | Shetty | .................... | A61M 5/28 |
| 2016/0317752 A1* | 11/2016 | Cowe | ..................... | A61M 5/20 |
| 2017/0079911 A1* | 3/2017 | Ayala | ..................... | A61K 9/02 |

\* cited by examiner

DRUG DELIVERY DEVICE

PRIORITY

This application claims priority to Indian Provisional Application No. 201621010632, filed Mar. 28, 2016, the contents of which are incorporated by reference herein."

FIELD OF THE DISCLOSURE

The present disclosure relates to syringe devices for delivering a dosage of a drug to a patient.

BACKGROUND

In some treatments, patients need to be administered medicaments from an applicator by a health care provider, sometimes at home. The amount of medicament required to be administered to a patient, depends upon factors such as, the size and weight of the patient, the age and sex of the patient, the patient age group, i.e., whether the patient is a child or an adult, and the like.

In order to administer the proper dose to a patient, applicators are required to be metered to deliver a desired dose volume of the medicament from the entire dose volume. Alternatively, the health care provider needs to adjust the dose volume to be delivered.

Presently available options have certain drawbacks. In accordance with one available embodiment, several versions of the applicator device are manufactured, with each version having a different volume of the medicament. For each dose a different version of the device is used. This requires the distributor of the device and the pharmacist to use up a relatively large shelf space for maintaining the inventory of multiple versions of the device containing different amounts of the drug.

In accordance with another available option, where variable doses can be set, a health care provider, who is less educated in the field, is apt to make an error in setting the proper dosage. This can result in disastrous results and even lead to a medical emergency.

U.S. Pat. No. 7,329,241 relates to a drug delivery system for administering an adjustable preset dose of a drug such as diazepam to a patient. This device is available in the U.S. market under the trade name Diastat Acudial. The patent suggests an apparatus for dispensing a dose of a drug in a syringe having a plunger, comprising an outer housing and an inner housing adapted for encircling the syringe, such that the inner housing is positioned within the outer housing to set the dose of the drug and a locking assembly. This patent further envisages a dosage indicator disposed on the inner housing and a window for viewing the dosage indicator on the outer housing. Also is suggested, a locking assembly connected to the inner housing and the outer housing for fixing the relative positions of the inner housing and the outer housing such that the dosage indicator is viewable through the opening in the outer housing.

U.S. Patent Application No. 20100305515 ("the '515 application") discloses a drug delivery system for administering an adjustable preset dose of a drug or a nutritional supplement to a human or veterinary patient or for delivering, for example, fertilizer in agricultural use. The '515 application relates to an apparatus for dispensing a dose of a drug in a syringe having a plunger with multiple flanges, and locking assembly. Also, the suggested syringe is bulky and has complex and delicate moving parts which can be difficult to assemble and expensive to manufacture.

Thus there is still a need for a syringe device with which an accurate amount a liquid can be discharged through a simple operation which avoids the above disadvantages. In particular, syringe device should comprise relatively few and simple parts, should not require excessive amounts of space, should be robust and at the same time should provide reliable fluid discharge.

OBJECTS OF THE DISCLOSURE

An object of the present disclosure is to overcome at least some of the drawbacks of the aforementioned syringe.

Another object of the present disclosure is to provide a syringe device for delivery of an adjustable preset dose of medicaments.

Another object of the present disclosure is to provide accurate adjusting of the dose of the medicament or setting the dose of a medicament.

These and other advantages of the present disclosure will become readily apparent from the following description read in conjunction with the accompanying drawings.

SUMMARY OF THE DISCLOSURE

The following presents a simplified summary of the disclosure in order to provide a basic understanding of some aspects of the disclosure. This summary is not an extensive overview of the present disclosure. It is not intended to identity the key/critical elements of the disclosure or to delineate the scope of the disclosure. Its sole purpose is to present some concept of the disclosure in a simplified form as a prelude to a more detailed description of the disclosure presented later.

The present disclosure envisages a locking mechanism for an adjustable drag delivery device for delivering a specified dosage of a substance. The delivery system can be used to deliver, for example, a drug or a nutritional supplement to a human or veterinary patient.

In a general aspect, the present disclosure envisages a syringe device, comprising:
(a) an outer housing,
(b) a barrel,
(c) stopper, and
(d) a plunger with one or more grooves of variable length.

One embodiment of the present disclosure provides an apparatus for setting a dose of a drug in a syringe having a plunger, comprising an outer housing adapted for encircling the syringe, within the outer housing to set the dose of the drug.

In another embodiment, a dosage indicator is disposed on the outer housing which further comprises an opening for viewing the dosage indicator.

In yet another embodiment, a locking assembly may be connected to the outer housing for fixing the relative positions of the plunger and the outer housing such that the dosage indicator is viewable through the opening in the outer housing.

In a further embodiment, dosage indicia may be disposed on the outer housing and may provide a predetermined number of dosages of the drug in increments ranging from approximately 0.1 ml to approximately 15 ml.

In yet another embodiment, a dosage indicator may provide a predetermined number of dosages of the drug in increments ranging from approximately 0.10 mg to approximately 100 mg.

In still one more embodiment, dosage indicia may be disposed on the plunger and may provide a predetermined number of dosages of the drug in increments ranging from approximately 0.1 ml to approximately 15 ml.

In yet another embodiment, a dosage indicator may provide a predetermined number of dosages of the drug in increments ranging from approximately 0.10 mg to approximately 100 mg.

In still another embodiment, a stopper may be attached to the outer housing for fixing at least one distance that the plunger can move within the syringe.

Particularly, the plunger may be provided with multiple grooves of variable length.

In another embodiment, a nozzle may be attached to the outer housing for the dispensing of the drug and material may be disposed on the exterior of the nozzle. Particularly, the material may comprise a lubricious material, such as a polymer material containing polytetrafluoroethylene. Still particularly, a removable covering may be attached to either the nozzle or the syringe.

In an embodiment, the outer housing may comprise two portions that are substantially cylindrical in shape.

In another embodiment, grooves may be disposed on the plunger, such that the grooves on the plunger and stopper engage each other and the relative axial positions of the grooves and stopper are adjustable by rotation of a ring relative to the outer housing. Typically, the grooves on the plunger may be predetermined such that a desired predetermined dosage may correspond to a predetermined amount of depression of the plunger relative to the outer housing.

In accordance with another aspect of the present disclosure, there is provided a method of adjusting the dosage dispensed from a syringe, the method comprising the following steps:
(a) holding the syringe with one hand,
(b) rotating a ring on the syringe with the other hand to establish a required dose; and
(c) locking the dose by pushing a stopper.

In an embodiment, the method may include displaying, through a display window, the dosage indicia.

In one embodiment, the syringe device may comprise an indexing mechanism for use with a medicament dispenser for indexing either the level of the medicament or the number of doses dispensed in a predetermined time period or both.

In another embodiment, a dosage indicia may have numbers or alphabets or alphanumerical indications which indicate either the level of the medicament or the number of dosages to be dispensed.

Numerous other advantages and features of the present disclosure will become readily apparent from the following detailed description and from the accompanying drawings.

BRIEF DESCRIPTION OF THE DRAWINGS

The following figures are illustrative of particular examples for enabling embodiments of devices and methods of the present disclosure, are descriptive of some of the embodiments and are not intended to limit the scope of the disclosure. The figures are not to scale (unless so stated) and are intended for use in conjunction with the explanations in the following detailed description. Wherever applicable, the words and phrases used herein should be understood and interpreted to have a meaning consistent with the understanding of those words and phrases by those skilled in the relevant art. Persons skilled in the art will appreciate that elements in the figures are illustrated for simplicity and clarity and may have not been drawn to scale. For example, the dimensions of some of the elements in the figure may be exaggerated relative to other elements to help to improve understanding of various exemplary embodiments of the present disclosure. Throughout the drawings, it should be noted that like reference numbers are used to depict the same or similar elements, features, and structures.

DETAILED DESCRIPTION

The following description with reference to the accompany drawings is provided to assist in a comprehensive understanding of exemplary embodiments of the disclosure. It includes various specific details to assist in that understanding but these are to be regarded as merely exemplary. Accordingly, those of ordinary skill in the art will recognize that various changes and modifications of the embodiments described herein can be made without departing from the scope and spirit of the disclosure. In addition, descriptions of well-known functions and constructions are omitted for clarity and conciseness.

The terms and words used in the following description are not limited to the bibliographical meanings, but, are merely used to enable a clear and consistent understanding of the disclosure. Accordingly, it should be apparent to those skilled in the art that the following description of exemplary embodiments of the present disclosure are provided for illustration purpose only and not for the purpose of limiting the disclosure as defined by the appended claims and their equivalents.

It is to be understood that the singular forms "a," "an," and "the" include plural references unless the context clearly dictates otherwise.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof.

Illustrative embodiments of the disclosure are described below. In the interest of clarity, not all features of an actual implementation are described in this specification. It will of course be appreciated that in the development of any such actual embodiment, numerous implementation-specific decisions should be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The syringe device of the present disclosure is illustrated below by way of example, with reference to FIGS. 1 to 8.

Figure 1:
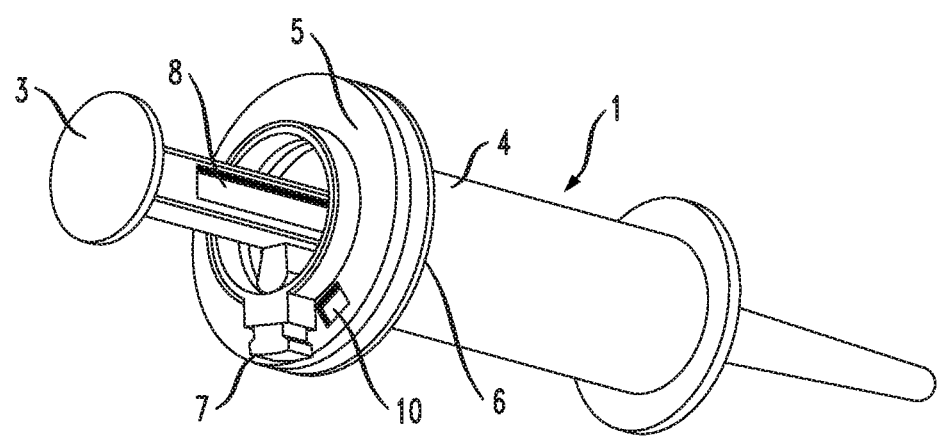
FIG. 1 illustrates a perspective view of a syringe device in accordance with one embodiment of the present disclosure.

A syringe device 1, as shown in FIG. 1, comprises a barrel, (not shown) which is a tubular housing in which a plunger 3 can be movably located. The barrel 2 has a proximal end for attachment of the plunger 3 and a distal end with a smaller opening for dispensing a dosage form. The barrel 2 is covered with an outer housing 4, which is non-movable with respect to barrel 2. The outer housing 4 may be a single unit or may be made up of two parts releasably or permanently attached with each other. Outer housing 4 may be in the general form of an elongated cylindrical barrel as is known in the art for the general shape of a syringe, although other forms for containing a fluid for delivery are also contemplated. The syringe device 1 further contains a ring 6 which may be releasably or fixedly attached to the barrel 2 of outer housing 4. The ring 6 is stationary with respect to the barrel and has a dosage indicia (not shown in figure). The syringe device 1 further comprises a ring 5 which may be releasably or fixedly attached to the ring 6. The releasable attachment may have snap fitting devices. The fixed attachment may have snap fitting devices or adhesive or ultrasonic welding or any other kind of welding or any other available technics known to the skilled artisan. The ring 5 has an opening for viewing the dosage Indicia present on ring 6 and another opening for the stopper 7. The plunger 3 can have one or more grooves 8 of variable length. As one skilled in the art will readily appreciate, the number of grooves can vary from case to case of the user, depending on the dosing requirements. The length of each of the grooves 8 corresponds to the dosage indicia.

Figure 2:
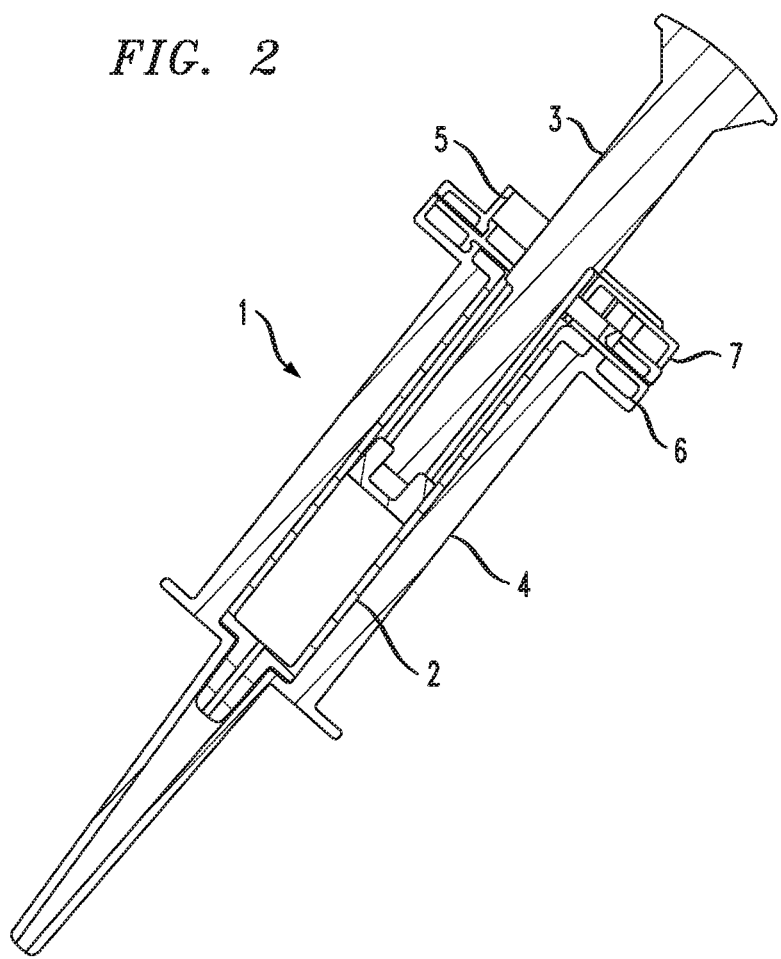
FIG. 2 illustrates a longitudinal cross sectional view of the syringe device of FIG. 1 through a stopper.

FIG. 2 shows a longitudinal cross-section through the stopper 7 of the syringe device 1. The barrel 2 is covered with an outer housing 4. FIG. 2 farther shows a cross sectional view of the plunger 3, ring 5 and ring 6. A stopper 7 is also shown in the figure. The plunger 3 has grooves (not shown). The stopper 7 and grooves 8 may be of various sizes and shapes.

Figure 3:
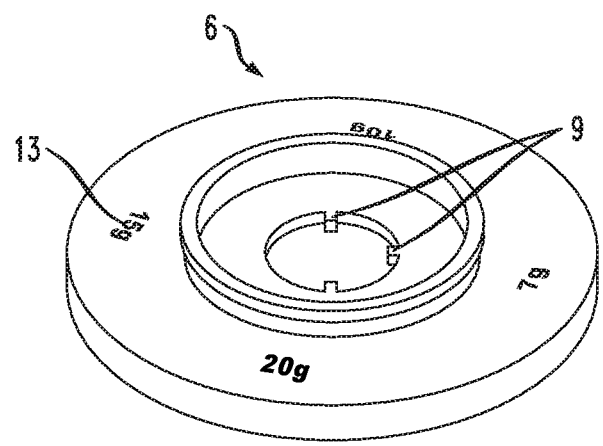
FIG. 3 illustrates a perspective view of an indexing ring of the syringe device of FIG. 1.

FIG. 3 shows a perspective view of an Indicia Ring 6. The Indicia Ring 6 may further comprise a cam 9 on the inner circumference and an indicia 13. The purpose of cam 9 is to restrict the rotational movement of the plunger 3 by engaging with the grooves 8 on the plunger. Single or multiple cams 9 may be present on the inner circumference of the ring 6.

Figure 4:
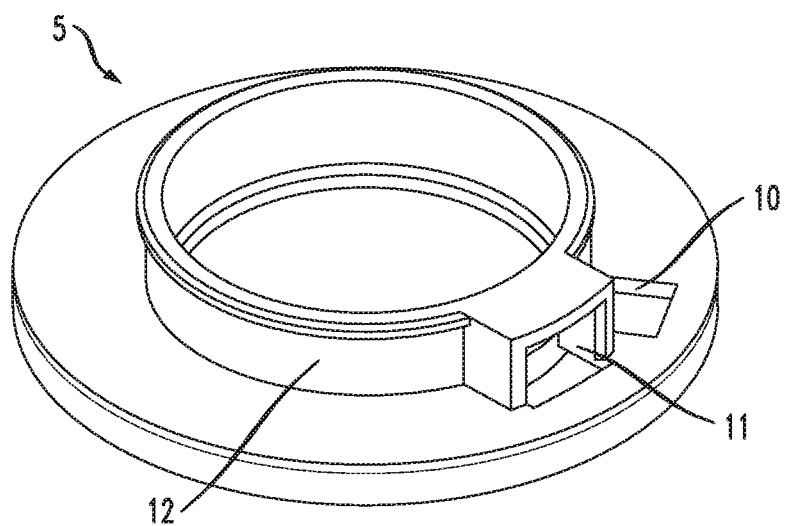
FIG. 4 illustrates a perspective view of an indexing ring with openings, of the syringe device of FIG. 1.

FIG. 4 shows a perspective view of ring 5, with multiple openings. The opening 10 may be present on the planar surface of ring 5 for the purpose of viewing the indicia present on the ring 6. An opening 11 may be present on the rim 12 of ring 5. The opening 11 may act as housing for the stopper 7.

Figure 5:
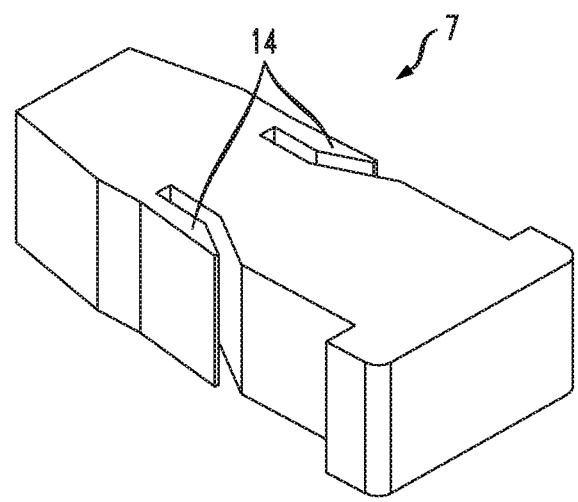
FIG. 5 illustrates a perspective view of a stopper of the syringe device of FIG. 1.

FIG. 5 shows a perspective view of a stopper 7. The stopper 7 may have a single or multiple cantilevers 14 for the purpose of snap fitting within the stopper opening 11. The stopper 7 may limit the vertical motion of the plunger 3 by engaging with a selected plunger groove 8. In an alternative embodiment for snap fitting, it is contemplated that different arrangements may be present instead of cantilevers.

Figure 6:
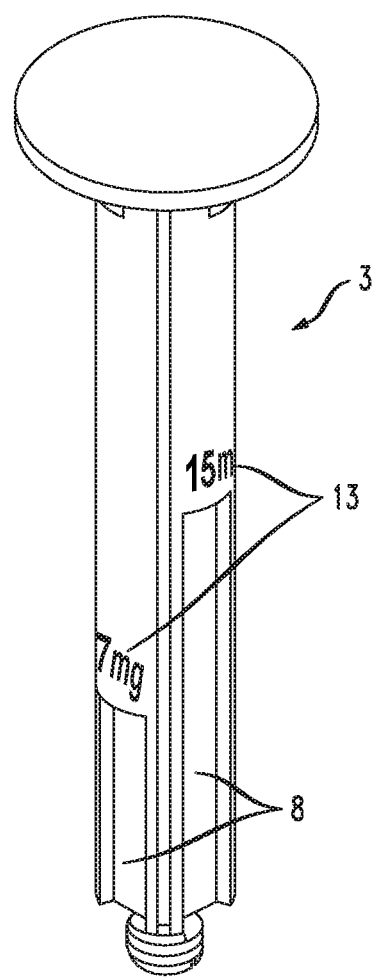
FIG. 6 illustrates a perspective view of a plunger of the syringe device of FIG. 1.

FIG. 6 shows a perspective view of a plunger 3. The plunger 3 may have a single groove or multiple grooves 8. The multiple grooves 8 may be of variable length. The length of the grooves may depend on the dose of the medicament, which may be shown by dosage indicia 13. The dosage indicia 13 may be present above the respective grooves towards the proximal end of the plunger 3.

Figure 7A:
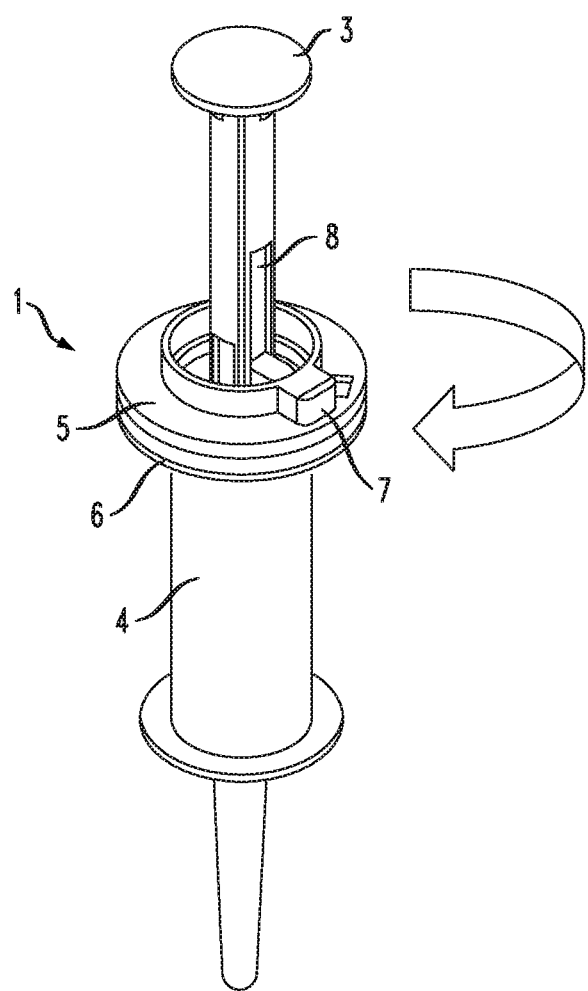
FIG. 7a illustrates a perspective view of the syringe device of FIG. 1 with the direction of rotation.
Figure 7B:
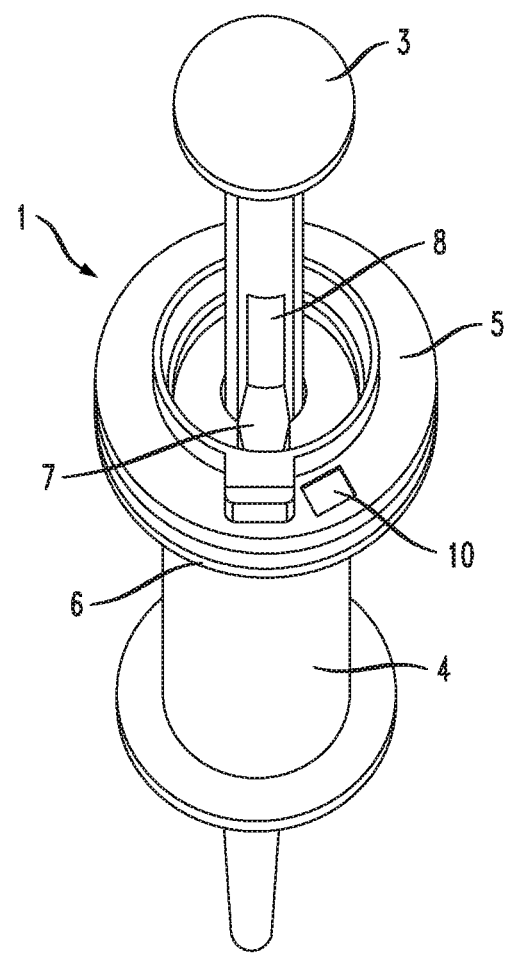
FIG. 7b illustrates a perspective elevated view of the syringe device of FIG. 1 showing a stopper and a dosage indicia.
Figure 7C:
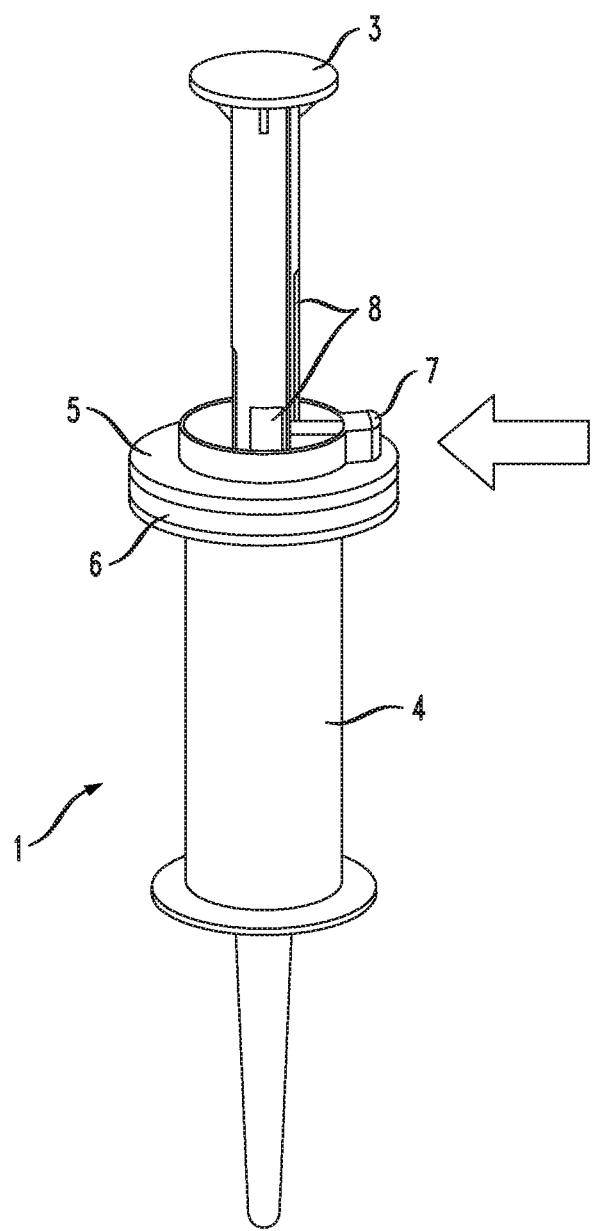
FIG. 7c illustrates a side perspective view of the syringe device of FIG. 1 showing a depressed stopper.
Figure 7D:
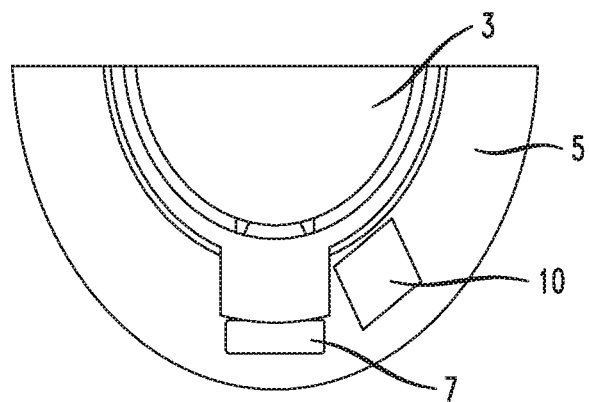
FIG. 7d illustrates a top view of a locking mechanism showing a depressed stopper and a dosage indicia.

FIGS. 7a, 7b, 7c and 7d are different views of the syringe device 1 showing some of the positions of the ring 5 and stopper 7. FIG. 7a is a perspective view of the syringe device 1. FIG. 7b is an elevated perspective of the syringe device 1. FIG. 7c shows a side view of the syringe device 1. FIG. 7d shows a top view of the syringe device 1 showing the locking position of the stopper 7.

The stopper 7, plunger 3 with groove 8, ring 5 and ring 6 operatively connected to the barrel of outer housing 4 are shown in FIG. 7a at a resting position. The ring 5 may be rotated clockwise or anticlockwise for selection of the required dose. The dose may be confirmed by viewing the dosage indicia through the opening 10 (not shown in the figure).

FIG. 7b shows the syringe device 1 in dial position of the ring 5 with respect to ring 6 and outer housing 4 which are stationary. The dosage indicium may be seen through the opening 10. The stopper 7 is aligned with the plunger groove 8. The plunger 3 remains in resting position.

FIG. 7c of the syringe device 1 shows the stopper 7, "depressed", to its maximum extension in the groove 8. Alternatively, the stopper 7 may contain locking levers which engage with the ring 5 and thus lock the stopper 7 with groove 8 and thus limits traveling length of the barrel 3. It also limits rotational movement of ring 5 with respect to ring 6 and outer housing 4.

FIG. 7d shows a top view of the syringe device 1 showing the locking position of the stopper 7. It also shows the top view of barrel 3, ring 5 and opening 10 for indicia.

Figure 7E:
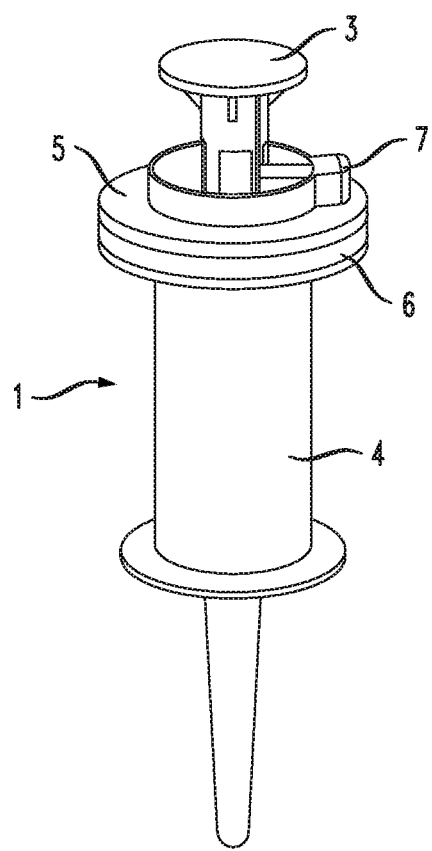
FIG. 7e illustrates a side perspective view of the syringe device of FIG. 1 showing a depressed plunger up to maximum extension.

A depressed position of the plunger 3 of syringe device 1 is shown in FIG. 7e. The depression length of the plunger 3 depends on the length of the groove 8 and stopper 7. The stopper 7 engages with the groove 8, depending upon the selected dose, which limits the maximum depression of the plunger 3 in barrel 2 (not shown) of outer housing 4. The selected dose may be seen through the opening 10 (not shown), present on ring 5, from the dosage indicia, which are present on ring 6.

Figure 8:
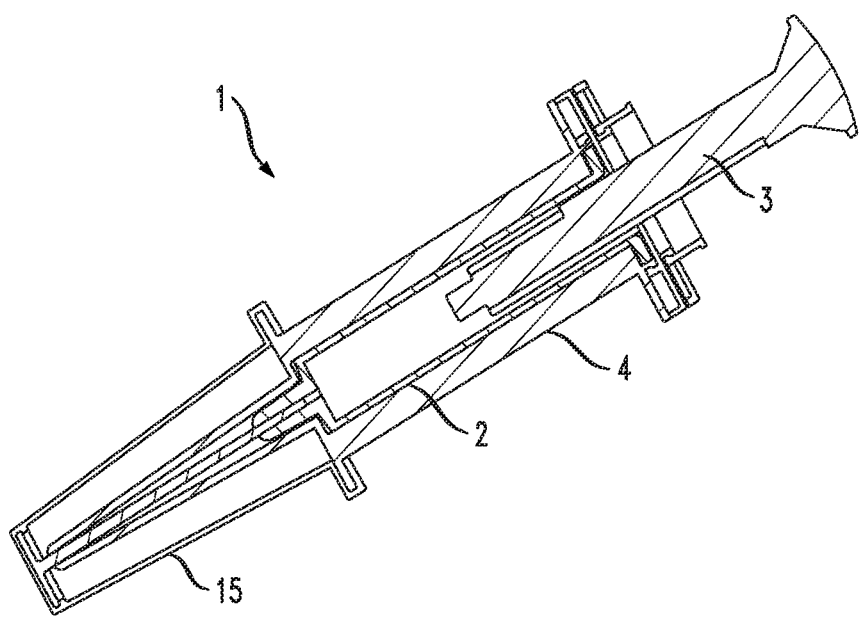
FIG. 8 illustrates a longitudinal cross sectional view of alternate embodiment of the syringe device through removable cap.

In another alternative embodiment of syringe device 1, in which the barrel 2 may contain a removable cap 15, opposite to the opening to the plunger 3, as shown in FIG. 8. The removable cap may be an integral part of the outer housing 4 or may be releasably attached to the barrel 2.

Although the disclosure herein has been described with reference to particular embodiments, it is to be understood that these embodiments are merely illustrative of the principles and application of the present disclosure. It is therefore to be understood that numerous modifications may be made to the illustrative embodiments.

What is claimed is:

1. A syringe device, comprising:
   an outer housing defining a longitudinal axis;
   a barrel disposed in the outer housing;

a stopper; and a plunger with two or more grooves disposed in two or more different axial positions in an outer surface of the plunger;

wherein the stopper is attached to the outer housing and configured to rotate to the different axial positions when in a resting position of the stopper and is moved radially inwardly relative to the longitudinal axis to a locking position of the stopper to engage with a selected one of the two or more grooves for fixing a distance that the plunger is able to move within the syringe device; and wherein the fixed distance that the plunger is able to move within the syringe is based at least in part on a length of the selected groove, the length of the selected groove corresponding to a predetermined amount of depression of the plunger relative to the outer housing for a predetermined dosage.

2. The syringe device of claim 1, wherein:

a first one of the two or more grooves has a first length corresponding to a first predetermined amount of depression of the plunger relative to the outer housing for a first predetermined dosage; and at least a second one of the two or more grooves has a second length corresponding to a second predetermined amount of depression of the plunger relative to the outer housing for a second predetermined dosage.

3. The syringe device of claim 1, wherein the stopper comprises a locking mechanism for engaging the stopper with the selected groove of the plunger, the locking mechanism comprising at least one locking lever that engages with the selected groove to limit a traveling length of the barrel and rotational movement of the stopper.

4. The syringe device of claim 1, further comprising a locking assembly operatively connected to the outer housing for fixing the relative positions of the plunger and the outer housing such that a dosage indicator is viewable through an opening in the outer housing.

5. The syringe device of claim 1, used to deliver a drug or a nutritional supplement to a human or veterinary patient.

6. The syringe device of claim 1, further comprising a dosage indicator which is disposed on at least one of the outer housing and the plunger.

7. The syringe device of claim 6, further comprising an opening for viewing the dosage indicator.

8. The syringe device of claim 6, wherein the dosage indicator has at least one of numbers, alphabets, and alphanumerical indications which indicate at least one of a level of a medicament or a number of dosages to be dispensed.

9. The syringe device of claim 6, wherein the dosage indicator is disposed on the outer housing and provides a predetermined number of dosages of a drug in increments ranging from about 0.1 ml to about 15 ml.

10. The syringe device of claim 6, wherein the dosage indicator is disposed on the outer housing and provides a predetermined number of dosages of a drug in increments ranging from about 0.10 mg to about 100 mg.

11. The syringe device of claim 6, wherein the dosage indicator is disposed on the plunger and provides a predetermined number of dosages of a drug in increments ranging from about 0.1 ml to about 15 ml.

12. The syringe device of claim 6, wherein the dosage indicator is disposed on the plunger and provides a predetermined number of dosages of a drug in increments ranging from about 0.10 mg to about 100 mg.

13. The syringe device of claim 1, wherein the one or more grooves are disposed on the plunger such that the selected groove on the plunger and the stopper engage each other by rotation of a ring relative to the outer housing.

14. The syringe device of claim 1, wherein the stopper has one or more cantilevers.

15. The syringe device of claim 14, further comprising a nozzle, wherein a material disposed on an exterior of the nozzle comprises a lubricious material.

16. The syringe device of claim 1, wherein the outer housing comprises two portions that are substantially cylindrical in shape.

17. A syringe device for setting a dose of a drug, comprising:

a syringe comprising a plunger, the plunger comprising a plurality of grooves disposed in an outer surface of the plunger at different axial positions thereof, the plurality of grooves comprising a first groove having a first length and at least a second groove having a second length different than the first length;

a stopper; and an outer housing adapted for encircling the syringe within the outer housing to set the dose of the drug by engaging the stopper with a selected one of the plurality of grooves by radially moving the stopper from a resting position to a locking position.

18. The syringe device of claim 17, further comprising a ring configured for rotating the stopper to the different axial positions.

19. The syringe device of claim 18, wherein the ring comprises an opening for viewing a dosage indicator for the selected groove, the dosage indicator being disposed on at least one of the outer housing and the plunger.

20. A method of adjusting a dosage dispensed from a syringe device, wherein the method comprises the following steps:

rotating a stopper attached to an outer housing of the syringe device to a selected one of at least two different axial positions for fixing a distance that a plunger is able to move within the syringe device, each of the different axial positions being associated with a respective one of two or more grooves disposed in an outer surface of the plunger of the syringe device; and engaging the stopper with a selected one of the two or more grooves corresponding to the selected axial position by radially moving the stopper from a resting position to a locking position, a length of the selected groove corresponding to a predetermined amount of depression of the plunger relative to the outer housing for a desired predetermined dosage.

\* \* \* \* \*